United States Patent
Coy-Herbert

(10) Patent No.: US 6,497,234 B1
(45) Date of Patent: Dec. 24, 2002

(54) HERBAL COMPOSITION AS A SUBSTITUTE FOR TOBACCO

(76) Inventor: Pamela Coy-Herbert, P.O. Box 290, Durango, CO (US) 81303

( * ) Notice: Subject to any disclaimer, the term of this patent is extended or adjusted under 35 U.S.C. 154(b) by 12 days.

(21) Appl. No.: 09/721,829

(22) Filed: Nov. 22, 2000

Related U.S. Application Data

(60) Provisional application No. 60/167,056, filed on Nov. 22, 1999.

(51) Int. Cl.$^7$ .......................... A61K 35/78; A24B 15/00
(52) U.S. Cl. ...................... 131/352; 131/359; 424/725; 424/40; 424/195.17; 424/747; 424/774; 424/773
(58) Field of Search ................................ 131/352, 359, 131/369; 424/40, 195.17, 725, 747, 774, 773

(56) References Cited

U.S. PATENT DOCUMENTS

| | | | | |
|---|---|---|---|---|
| 4,269,204 A | | 5/1981 | Yamaguchi | 131/341 |
| 4,696,315 A | | 9/1987 | Summers | 131/359 |
| 5,119,834 A | | 6/1992 | Shannon et al. | 131/194 |
| 5,135,010 A | | 8/1992 | Fan | 131/359 |
| 5,992,421 A | * | 11/1999 | Bae | 131/369 |
| 6,045,825 A | | 4/2000 | Cody | 424/451 |
| 6,063,401 A | | 5/2000 | Cody | 424/451 |

* cited by examiner

*Primary Examiner*—Steven P. Griffin
*Assistant Examiner*—Dionne A. Walls
(74) *Attorney, Agent, or Firm*—Stephen A. Slusher

(57) ABSTRACT

A composition for use as a tobacco substitute and as an aid in the cessation of tobacco use, containing a *Vebascum thapsus* component, an algae component, a *Medicago sativa* component, and a *Symphytum officinale* component, together with other optional components. Use of the composition of the present invention as a tobacco substitute, in cigarettes or pipes, produces a diminished desire for tobacco.

17 Claims, No Drawings

HERBAL COMPOSITION AS A SUBSTITUTE FOR TOBACCO

CROSS-REFERENCE TO RELATED APPLICATIONS

This application claims the benefit of the filing of U.S. Provisional Patent Application Serial No. 60/167,056, entitled Herbal Composition and Method as a Substitute for Tobacco, filed on Nov. 22, 1999, and the specification thereof is incorporated herein by reference.

BACKGROUND OF THE INVENTION

1. Field of the Invention (Technical Field)

The present invention relates to a mixture of herbs and other natural products that can be used as a healthy substitute for tobacco. The herbal composition of the present invention also alleviates the addictive effects of nicotine, and provides an aid to quit smoking tobacco-related products.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Smoking tobacco, and particularly cigarette smoking, is recognized as a substantial health factor, and a major risk factor in a variety of diseases, including coronary artery disease and a wide range of cancers. It is also recognized that nicotine, a constituent of tobacco, is highly addictive, making decreasing or ceasing to smoke tobacco-related products very difficult for a significant percentage of tobacco users.

At present there are several consumer products that help people overcome their addiction to nicotine found in all tobacco related products. One type of product includes a transdermal patch, which allows the person's body to slowly absorb a prescribed amount of nicotine over a given period. Little by little the dosage of nicotine in the patches is decreased until the person is no longer addicted. Once the physical addiction to nicotine is overcome, the person can more easily fight the psychological, associational and related desires to smoke.

Another type of product is sold in the form of a chewing gum containing nicotine. Thus, whenever a smoker has the urge to smoke, the smoker will chew the gum instead. However, the smoker still has to restrict the use of the gum in a manner that will eventually overcome the addiction.

There are substantial limitations and drawbacks to the various methods of nicotine-replacement therapy in current use. Orally ingested materials, including gums, have a bad taste, may lead to mouth ulcers, heartburn and other adverse consequences, and are highly dependent of the user following a specific regime. Other forms of oral administration can result in nausea, unpredictable nicotine blood levels and the like. Patches, including transdermal patches, and other topical applications of nicotine can cause skin irritation, and patches containing nicotine are known to cause pruritus.

Devices and methods involving nicotine therapy all necessarily depend on the use of nicotine, the substance causing addiction, to control nicotine craving or desire. This approach is thus susceptible to abuse, and users are known to become addicted to the use of gum, patches or the like, and not to decrease nicotine intake as instructed. In addition, users are known to concurrently use both tobacco, as in cigarettes, and nicotine therapy aids, such as gum or patches, thereby increasing the total intake of nicotine. Further, in such instances acute adverse medical consequences may result, including increased heart rate, increased blood pressure and other conditions associated with nicotine administration.

There are certain herbal preparations that are known to have been used as smoking materials, including use in non-tobacco cigarettes. For example, U.S. Pat. No. 5,135,010 discloses use of nicotine-free herbal compositions, used either as a substitute for or in combination with tobacco. This smoking composition may include *Laurus nobilis* and *Nelumbo garetin*. The use of herbal preparations as aids in cessation of tobacco use is taught in U.S. Pat. Nos. 6,045,825 and 6,063,401. These patents disclose use of herbs such as *Plantago major*, *Piper methysticum* and *Hypericum perforatum*.

The present invention removes approximately 25 to 90 percent or more of the craving a person would normally experience when that person attempts to reduce their use of nicotine containing products or stop using such products altogether. At the same time the invention will strengthen the person's immune system allowing that person to stop smoking tobacco with very little effort.

SUMMARY OF THE INVENTION (DISCLOSURE OF THE INVENTION)

The invention provides a composition for use as a tobacco substitute for aiding in the cessation of tobacco use, the composition including a *Vebascum thapsus* component, an algae component, a *Medicago sativa* component, and a *Symphytum officinale* component. The *Vebascum thapsus* component may be dried leaves of *Vebascum thapsus*, the algae component may be Laminaria, the *Medicago sativa* component may be dried leaves of *Medicago sativa* or may also be an aqueous concentrate of *Medicago sativa*, and the *Symphytum officinale* component may be dried root of *Symphytum officinale*. The composition may contain approximately equal quantities of each of the components by weight. The composition may further include cigarette paper, and may be formed into a cigarette. In this composition, the algae component and *Medicago sativa* component may be Wachters' Organic Sea Food No. 3.

A variety of other ingredients may be added to the composition, including *Cnicus benedictus*, *Centalla asiatica*, *Mentha peperita*, *Glycyrrhiza glabra*, *Eriodictyon californicum*, *Ilex paraguaiensis*, *Lobelia inflata*, or *Hypericum perforatum*, or a combination of any of the foregoing.

In an alternative embodiment, the invention provides a composition for use as a tobacco substitute for aiding in the cessation of tobacco use, the composition including a *Vebascum thapsus* component, an algae component, and a *Medicago sativa* component. This composition may further include *Cnicus benedictus*, *Centalla asiatica*, *Mentha peperita*, *Glycyrrhiza glabra*, *Eriodictyon californicum*, *hex paraguaiensis*, *Lobelia inflata*, or *Hypericum perforatum*, or a combination of any of the foregoing. Here too the algae component and *Medicago sativa* component may be Wachters' Organic Sea Food No. 3.

A primary object of the present invention is to provide the means to reduce the addictive affects of nicotine in tobacco smokers.

Another object of the invention is to provide a healthy alternative for people who decide to continue smoking.

A primary advantage of the present invention is that it provides a means for people to reduce their addiction for nicotine at relatively low cost.

Other objects, advantages and novel features, and further scope of applicability of the present invention will be set forth in part in the detailed description to follow, and in part will become, apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED EMBODIMENTS (Best Modes for Carrying out the Invention)

A number of herbs and other ingredients are employed in this invention, and are defined as follows:

Mullein includes *Verbascum thapsus*, and primarily the dried leaves of *Verbascum thapsus*.

Alfalfa includes *Medicago sativa*, and both dried leaves of *Medicago sativa* as well as the juice, extracts and concentrates of the juice or extracts of *Medicago sativa*.

Algae includes marine algae, and specifically brown algaes, including those from the Laminaria family, and green algaes. Algae is generally prepared in a dried formulation, but may be powdered or an extract.

Blessed thistle includes *Cnicus benedictus*.

Gota kola includes *Centalla asiatica*, also known as *Hydrocotyle asiatica*.

Peppermint includes *Mentha peperita*, and primarily the leaves of *Mentha peperita*.

Licorice includes *Glycyrrhiza glabra*, and primarily dried root of *Glycyrrhiza glabra*.

Yerba santa includes *Eriodictyon californicum*.

Yerba matte, also called yerba mate, includes *Ilex paraguaiensis*.

Comfrey includes *Symphytum officinale*, and primarily dried root of *Symphytum officinale*.

Lobelia, also called lobella, includes *Lobelia inflata*.

St. John's Wort includes *Hypericum perforatum*.

The present invention comprises a mixture of selected natural herbs and other natural products that a person smokes to help alleviate a smoker's addictive craving for nicotine containing products. The herbal composition comprises mullein leaves and a mixture comprising algae and/or other sea greens, and alfalfa and/or alfalfa extracts ("sea green mixture"). In a preferred embodiment, Wachters' Organic Sea Food No. 3 ("Wachters") obtained from Wachters' Organic Sea Products Corp. of San Francisco, Calif. is used as the source of the algae and alfalfa products. Other ingredients found in Wachters', include chlorophyll, carotene, cereal solids, natural mint, vitamin C, fructose, rose hips, acerola, lemon bioflavinoids, hesperidin complex, rulin, natural orange flavor, and calcium and potassium plant sweetener.

In a preferred embodiment, the composition comprises a sea green mixture or a Wachters' type mixture, mullein leaves and comfrey root. This may include approximately equal quantities, by weight, of algae, alfalfa leaves, mullein leaves and comfrey root. Other components can include blessed thistle, gota kola, lobelia or St. John's wort, as well as any one or more of flavoring components, including peppermint leaves, licorice root, yerba santa, and yerba matte.

In one embodiment, the composition comprises approximately 5 to 40 percent by weight, and preferably 10 to 25 percent by weight of sea green mixture or a Wachters' type mixture and approximately 5 to 40 percent by weight, and preferably 10 to 25 percent by weight of mullein leaves. The composition further comprises blessed thistle and/or gota kola. In the preferred embodiment, the composition comprises approximately 5 to 40 percent by weight, and preferably 10 to 25 percent by weight of blessed thistle and/or approximately 5 to 40 percent by weight, and preferably 10 to 25 percent by weight of gota kola. The composition further comprises a natural flavoring selected from the following group; peppermint leaves, licorice root, licorice spice tea mix, yerba santa, yerba matte, and any combination thereof. The flavorings of the composition comprise approximately 10 to 40 percent by weight, and preferably 10 to 25 weight percent. The composition may also include at least one of the following; comfrey root, licorice root, lobelia, and St. John's wort.

The herbal components generally are available individually whole, sliced, crushed, powdered, or extracts, etc., and are mixed either manually or automatically with a common mixer hopper according to selected weight compositions. The selected compositions are provided in packaging known in the art for tobacco products. Alternatively, a user can either roll the user's own herbal cigarettes, or can use a commercially available cigarette roller device. In addition, a user may employ a pipe, including a small pipe, to smoke the herbal composition.

In another embodiment of the invention, the composition comprises approximately 5 to 20 percent by weight, and preferably 8 to 15 weight percent sea green mixture or a Wachters' type mixture, approximately 5 to 20 percent by weight, and preferably 8 to 15 weight percent mullein leaves, approximately 5 to 20 percent by weight, and preferably 8 to 15 weight percent blessed thistle, approximately 5 to 20 percent by weight, and preferably 8 to 15 weight percent gota kola, approximately 5 to 20 percent by weight, and preferably 8 to 15 weight percent yerba matte, approximately 5 to 20 percent by weight, and preferably 8 to 15 weight percent lobelia, approximately 5 to 20 percent by weight, and preferably 8 to 15 weight percent St. John's wort, approximately 5 to 20 percent by weight, and preferably 8 to 15 weight percent licorice root, approximately 5 to 20 percent by weight, and preferably 8 to 15 weight percent comfrey root, and approximately 5 to 20 percent by weight, and preferably 8 to 15 weight percent peppermint leaves.

Another embodiment of the invention comprises approximately 5 to 20 percent by weight, and preferably 8 to 15 weight percent sea green mixture or a Wachters' type mixture, approximately 5 to 20 percent by weight, and preferably 8 to 15 weight percent mullein leaves, approximately 5 to 20 percent by weight, and preferably 8 to 15 weight percent blessed thistle, approximately 5 to 20 percent by weight, and preferably 8 to 15 weight percent gota kola, approximately 5 to 20 percent by weight, and preferably 8 to 15 weight percent yerba santa, approximately 5 to 20 percent by weight, and preferably 8 to 15 weight percent lobelia, approximately 5 to 20 percent by weight, and preferably 8 to 15 weight percent St. John's wort, approximately 5 to 20 percent by weight, and preferably 8 to 15 weight percent licorice root, approximately 5 to 20 percent by weight, and preferably 8 to 15 weight percent comfrey root approximately 5 to 20 percent by weight, and preferably 8 to 15 weight percent licorice spice, and approximately 5 to 20 percent by weight, and preferably 8 to 15 weight percent peppermint leaves.

Another embodiment of the invention comprises approximately 5 to 20 percent by weight, and preferably 8 to 15 weight percent sea green mixture or a Wachters' type mixture, approximately 5 to 20 percent by weight, and preferably 8 to 15 weight percent mullein leaves, approximately 5 to 20 percent by weight, and preferably 8 to 15 weight percent blessed thistle, approximately 5 to 20 percent by weight, and preferably 8 to 15 weight percent gota kola, approximately 5 to 20 percent by weight, and preferably 8 to 15 weight percent licorice spice, approximately 5 to 20 percent by weight, and preferably 8 to 15 weight percent St. John's wort, approximately 5 to 20 percent by weight, and preferably 8 to 15 weight percent licorice root, approximately 5 to 20 percent by weight, and preferably 8 to 15 weight percent comfrey root, and approximately 5 to 20 percent by weight, and preferably 8 to 15 weight percent peppermint leaves.

Another embodiment of the invention comprises approximately 5 to 20 percent by weight, and preferably 8 to 15 weight percent sea green mixture or a Wachters' type mixture, approximately 5 to 20 percent by weight, and preferably 8 to 15 weight percent mullein leaves, approximately 5 to 20 percent by weight, and preferably 8 to 15 weight percent blessed thistle, approximately 5 to 20 percent by weight, and preferably 8 to 15 weight percent gota kola, approximately 5 to 20 percent by weight, and preferably 8 to 15 weight percent yerba santa, approximately 5 to 20 percent by weight, and preferably 8 to 15 weight percent licorice spice, approximately 5 to 20 percent by weight, and preferably 8 to 15 weight percent St. John's wort, approximately 5 to 20 percent by weight, and preferably 8 to 15 weight percent licorice root, approximately 5 to 20 percent by weight, and preferably 8 to 15 weight percent comfrey root, a nd approximately 5 to 20 percent by weight, and preferably 8 to 15 weight percent peppermint leaves.

Another embodiment of the invention comprises approximately 5 to 20 percent by weight, and preferably 8 to 15 weight percent sea green mixture or a Wachters' type mixture, approximately 5 to 20 percent by weight, and preferably 8 to 15 weight percent mullein leaves, approximately 5 to 20 percent by weight, and preferably 8 to 15 weight percent blessed thistle, approximately 5 to 20 percent by weight, and preferably 8 to 15 weight percent gota kola, approximately 5 to 20 percent by weight, and preferably 8 to 15 weight percent St. John's wort, approximately 5 to 20 percent by weight, and preferably 8 to 15 weight percent licorice root, approximately 5 to 20 percent by weight, and preferably 8 to 15 weight percent comfrey root, and approximately 5 to 20 percent by weight, and preferably 8 to 15 weight percent peppermint leaves.

Another embodiment of the invention comprises, in lieu of the described Wachters' type mixture, a mixture consisting of algae and alfalfa. The algae and alfalfa may be in approximately equal quantities by volume or by weight, both being dried preparations. Alternatively, the alfalfa component may include a concentrate of an alfalfa juice or extract.

In any embodiment of the invention, it is also possible to include ascorbic acid or vitamin C, including herbal or other organic materials rich in vitamin C. In one embodiment, there is between about 50 mg and 100 mg of vitamin C for each level teaspoon of the combination of algae and alfalfa in the preparation.

An embodiment containing at least a Vebascum thapsus component, an algae component, a Medicago sativa component, and a Symphytum officinale component will provide the user with a decreased craving or desire for tobacco, and further provides healing benefits to ameliorate the deleterious effects of tobacco use. Such healing benefits include healing of the lungs and general strengthening of the immune system.

EXAMPLE 1

An herbal composition was made of equal parts by weight of the following; Wachters', mullein leaves, blessed thistle, gota kola, yerba matte, lobelia, St. John's wort, licorice root, comfrey root, and peppermint leaves.

EXAMPLE 2

An herbal composition was made of equal parts by weight of the following; Wachters', mullein leaves, blessed thistle, gota kola, yerba sante, lobelia, St. John's wort, licorice root, comfrey root, licorice spice, and peppermint leaves.

EXAMPLE 3

An herbal composition was made of equal parts by weight of the following; Wachters', mullein leaves, blessed thistle, gota kola, St. John's wort, licorice root, comfrey root, licorice spice, and peppermint leaves.

EXAMPLE 4

An herbal composition was made of equal parts by weight of the following; Wachters', mullein leaves, blessed thistle, gota kola, yerba sante, St. John's wort, licorice root, comfrey root, licorice spice, and peppermint leaves.

EXAMPLE 5

An herbal composition was made of equal parts by weight of the following; Wachters', mullein leaves, blessed thistle, gota kola, St. John's wort, licorice root, comfrey root, and peppermint leaves.

EXAMPLE 6

An herbal composition is made of equal parts by weight of the following; algae, mullein leaves, alfalfa leaves, blessed thistle, gota kola, St. John's wort, licorice root, and comfrey root.

EXAMPLE 7

An herbal composition was made of equal parts by weight of the following; Wachters', mullein leaves, blessed thistle, gota kola, yerba sante, lobelia, St. John's wort, licorice root, comfrey root, licorice spice, and peppermint leaves.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A composition for use as a tobacco substitute for aiding in the cessation of tobacco use, comprising:

a *Vebascum thapsus* component;

an algae component;

a *Medicago sativa* component; and a *Symphytum officinale* component.

2. The composition of claim 1, wherein the *Vebascum thapsus* component comprises dried leaves of *Vebascum thapsus*.

3. The composition of claim 1, wherein the algae component comprises Laminaria.

4. The composition of claim 1, wherein the *Medicago sativa* component comprises dried leaves of *Medicago sativa*.

5. The composition of claim 1, wherein the *Medicago sativa* component comprises an aqueous concentrate of *Medicago saliva*.

6. The composition of claim 1, wherein the *Symphytum officinale* component comprises dried root of *Symphytum officinale*.

7. The composition of claim 1, wherein the composition contains approximately equal quantities of each of the components by weight.

8. The composition of claim 1, further comprising cigarette paper and formed into a cigarette.

9. The composition of claim 1, further comprising *Cnicus benedictus*.

10. The composition of claim 1, further comprising *Centalla asiatica*.

11. The composition of claim 1, further comprising *Mentha peperita*.

12. The composition of claim 1, further comprising *Glycyrrhiza glabra*.

13. The composition of claim 1, further comprising *Eriodictyon californicum*.

14. The composition of claim 1, further comprising hex paraguaiensis.

15. The composition of claim 1, further comprising *Lobelia inflata*.

16. The composition of claim 1, further comprising *Hypericum perforatum*.

17. A composition for use as a tobacco substitute for aiding in the cessation of tobacco use, comprising;

a *Vebascum thapsus* component;

an algae component;

a *Medicago sativa* component; and at least one member selected from the group consisting of *Cnicus benedictus, Mentha peperita, Glycyrrhiza glabra, Eriodictyon californicum, Ilex paraguaiensis, Lobelia inflata*, and *Hypericum perforatum*.

* * * * *